United States Patent [19]

Ayres et al.

[11] Patent Number: 5,380,652

[45] Date of Patent: * Jan. 10, 1995

[54] DEVICE AND PROCEDURE FOR IDENTIFYING PATHOGENIC MICROORGANISMS

[76] Inventors: William W. Ayres, Box 305, Chalk Hill Rd., Chalk Hill, Pa. 15421; John Duda, 130 Creek Rd., Brownsville, Pa. 15417

[*] Notice: The portion of the term of this patent subsequent to Jul. 12, 2011 has been disclaimed.

[21] Appl. No.: 101,008

[22] Filed: Aug. 3, 1993

Related U.S. Application Data

[63] Continuation-in-part of Ser. No. 680,426, Apr. 4, 1991, Pat. No. 5,328,833.

[51] Int. Cl.$^6$ .......................... C12Q 1/00; C12Q 1/18; C12Q 1/14
[52] U.S. Cl. ........................................ 435/34; 435/29; 435/32; 435/36; 435/883; 435/882; 424/49; 424/52; 424/54
[58] Field of Search ............... 424/54, 52, 49; 435/29, 435/32, 34, 36, 883, 882

[56] References Cited

PUBLICATIONS

Lennette, et al. Manual of Clinical Microbiology, Third Edition American Society for Microbiology Washington, D.C. 1980 Ch 42 (pp. 453–458) Ch 44 (pp. 463–473), 1985.

Hugo, W. B. (Ed.) Inhibition and Destruction of the Microbiol Cell pp. 185–208 Academic Press, 1971.

*Primary Examiner*—William H. Beisner
*Assistant Examiner*—Jane Williams
*Attorney, Agent, or Firm*—James J. Brown

[57] ABSTRACT

Pathogenic microorganisms such as *Staphylococcus aureus* are differentiated and identified by observing the selective inhibition of the microorganism which occurs when it is contacted with Alphazurine A dye.

3 Claims, No Drawings

DEVICE AND PROCEDURE FOR IDENTIFYING PATHOGENIC MICROORGANISMS

CROSS-REFERENCE TO RELATED APPLICATIONS

This application is a continuation-in-part of application Ser. No. 07/680,426 filed Apr. 4, 1991, now U.S. Pat. No. 5,328,833.

BRIEF DESCRIPTION OF THE INVENTION

The present invention relates to a device and procedure for the clinical differentiation and identification of specific pathogenic microorganisms. More particularly the present invention is directed to a device and procedure for distinguishing and identifying *Staphylococcus aureus* in clinical environments.

BACKGROUND OF THE INVENTION

The staphylococci are by far the commonest cause of skin infections such as boils, abscesses, carbuncles and similar suppurative processes in man. They are primarily significant as pathogens. They can be grown on culture media, such as agar or meat extract media, and the individual colonies are circular with entire edges. The pathogenic forms, that is, those isolated from suppurative processes, usually are *Staphylococcus aureus*.

Staphylococci ferment mannitol with the formation of acid, the latter being detected by a decrease in pH of the media, as evidenced by color change of a pH indicator such as brom thymol blue, brom cresol purple, or phenol red.

Pathogenic staphylococci, that is, the *Staphylococcus aureus*, also cause clotting of decalcified blood plasma due to the production of staphylocoagulase, an active clotting agent. There is a high correlation between staphylococcal virulence for man and staphylocoagulase production. Coagulase-positive bacteria are usually virulent.

Plasma clotting (i.e., staphylocoagulase activity) can be demonstrated by mixing a bacterial culture with decalcified plasma, human or rabbit, incubating the plasma and observing clotting. The simple slide method is often used for qualitative purposes; the bacteria are suspended in a drop of plasma and observed on a slide for clumping.

In the treatment of wounds and similar skin lesions it is often desirable, and sometimes necessary, to identify the microorganisms in the wound or lesion in an agar or other medium and the microorganisms developed therein. It is therefore desirable to be able to identify *Staphylococcus aureus* promptly and accurately so that appropriate treatment can be instituted without delay. For this reason it is desirable to have a culture medium, and a material which inhibits the growth of *Staphylococcus aureus* and allows the rapid growth of most other microorganisms and thus allows rapid and accurate identification of coagulase positive organisms, mainly *Staphylococcus aureus* if present in the wound or lesion.

As discussed above, two of the most widely used tests for identifying staphylococci are the coagulase production test and the mannitol fermentation test. Most strains of *Staphylococcus aureus* isolated from human lesions are coagulase-positive and mannitol-positive. Coagulase-negative and mannitol-negative staphylococci, i.e. *S. epidermidis* and *S. saprophyticus* are most frequently considered to be less pathogenic. Positive reactions to both the coagulase production and mannitol fermentation tests are an indication of the pathogencity of the staphylococci. Negative reactions to both tests indicate that the isolate has less clinical significance. Classical tests for coagulase production are performed routinely by the so-called "tube" method which measures free coagulase production or by the so-called "slide" technique which measures bound coagulase either on or in the cell wall of the organism. The tube method and the slide technique are described in the publications J. Bact. 41:431–440 (1941) and Medical Microbiology, T. Cruickshank, pages 137–138, published by Willies and Wilkins Company, 11th edition, 1965, respectively. In these test, both rabbit plasma and human plasma have been used as the substrate.

Mannitol Salt Agar is used as a selective medium for the isolation of pathogenic staphylococci. This medium is described in J. Bact. 50:201–203 (1945). Due to the presence of 7.5% sodium chloride therein, growth of most bacteria, other than staphylococci, is inhibited on this medium. When the medium is inoculated with a material containing staphylococci and incubated for a period of 36 hours at a temperature of 370° C., mannitol-fermentation staphylococci grow luxuriantly, surrounded by yellow zones. In contrast, mannitol-non fermentation staphylococci produce small colonies, surrounded by red or purple zones. Positive identification of an unknown specimen as pathogenic can require as long as five days when conventional coagulase production and mannitol fermentation tests are employed.

A solid growth medium which is suitable for the visual identification of pathogenic staphylococci from initial cultures is described in the publication Am. J. Clin. Path. 32: 192–194 (August 1959). Some measure of success has been achieved using this medium. However, it has been found that other bacteria which produce coagulase, grow on this medium.

DESCRIPTION OF THE PRIOR ART

U.S. Pat. No. 4,035,238 to Meyer et al describes a broth medium for the detection of *Staphylococcus aureus* which employs mannitol to promote growth of the microorganisms and potassium tellurite to inhibit growth of gram-negative organisms.

U.S. Pat. No. 3,597,32 1 to Kronish et al describes a diagnostic composition for differentiating staphylococci which detects the fermentation of mannitol and an agent which detects production of coagulase.

U.S. Pat. No. 3,4 16,998 to Streitfeld describes dried transparent agar sheets for detecting microorganisms such as *Staphylococcus aureus*.

U.S. Pat. No. 3,278,393 to Bahn et al describes selective culture mediums for distinguishing *Staphylococcus aureus* and *Pseudomonas aeruginosa* from non-pathogenic microorganisms.

Green, Floyd J. The Sigman-Aldrich HANDBOOK of STAINS, Dyes and Indicators 1990 Published by Sigmna-Aldrich Corporation Page 87.

Loos, W. E. and Joregensen, 1985, Page 145 and 147. In E. H. Lennette, Al Balows, W. H. Hauser, Jr., H. J. Shadomy, (ed) Manual of Clinical Microbiology. 4th ed., American Society for Microbiology, Washington, D.C.

DETAILED DESCRIPTION OF THE INVENTION

In accordance with the present invention *Staphylococcus aureus* is clinically identified and differentiated from other staphylococci by selectively inhibiting growth of the microorganisms in a culture medium by incorporating into the medium Alphazurine A dye.

Alphazurine A is a bright greenish-blue anionic triphenylmethane dye with a high affinity for proteinaceous substrates and a week attraction to cellulosic materials.

This invention is based on the discovery that Alphazurine A dye inhibits the growth of *Staphylococcus aureus* when incorporated in a culture media and that *Staphylococcus aureus* is sensitive to Alphazurine A hereafter described as the Alphazurine effect. All staphylococci exhibiting the Alphazurine A effect are coagulase positive, representing an additional diagnostic characteristic for the identification for pathogenic staphylococci. The ability to clot plasma is the most widely used and generally accepted criterion for the frankly pathogenic Staphylococci, for example, *Staphylococcus aureus* in humans. Alphazurine A effect correlates 100% with positive coagulation tests.

In one embodiment of the invention, the Alphazurine dye is impregnated onto an absorbent material such as sterile paper to form "sensitivity discs" which are then placed on the surface of inoculated media and incubated to develop the culture. Where the inoculum is *Staphylococcus aureus*, the growth of the organism around the disc is inhibited, whereas other microorganisms are not so inhibited and generally flourish.

Other commonly used media can also be employed in accordance with the invention; and Alphazurine A can be introduced by various art recognized techniques into the culture.

When Alphazurine A dye is added to Petri plates containing cultures of *Staphylococcus aureus*, *Staphylococcus saprophyticus* and *Staphylococcus epidermidis* respectively, growth of *S. aureus* is inhibited while growth was not inhibited of *S. saprophyticus* and *S. epidermidis*.

Only one Staphylococcus, *Staphylococcus warneri* showed the Alphazurine A effect. *Staphylococcus warneri*, is a questionable or uncommon pathogen, and does not enter into the diagnosis of *Staphylococcus aureus* clinically.

All strains or *Staphylococcus aureus* which showed the alphzurine effect, were coagulase positive whereas all Staphylococci not showing the Alphazurine A effect were coagulase negative.

Alphazurine A sensitivity to *Staphylococcus aureus* can also be elicited on blood agar plates. As a result, a diagnosis of *Staphylococcus aureus* in accordance with the invention can be made on the primary inoculum from the infected site, which permits an early diagnosis.

On hundred twenty-six cultures of *Staphylococcus aureus* were studied and all showed Alphazurine sensitivity. Thirty-eight cultures of *Staphylococcus epidermidis* and twenty-eight cultures of *Staphylococcus saprophyticus* showed no sensitivity to Alphazurine A.

Thirty-eight cultures of gram negative bacteria also showed no Alphazurine A effect.

The following examples are illustrative of the invention using both paper discs impregnated with Alphazurine A and culture media containing Alphazurine A:

Alphazurine A was impregnated in paper discs. Mueller-Hinton agar media in culture plates was swabbed with a suspension in water of *Staphylococcus aureus*. Alphazurine A sensitivity disc was placed on the surface of the inoculated media and incubated at 370° C. for 24 hours. *Staphylococcus aureus* was sensitive to Alphazurine A and prevented the growth of *Staphylococcus aureus* in a zone around the sensitivity disc.

In addition to Mueller-Hinton media other culture media as Mannitol salt agar, Trypticase soy agar and Trypticase soy agar with 5 % sheep blood (Becton-Dickinson Microbiology Systems, Cockeysville, Md.) were used, and when streaked with *Staphylococcus aureus* showed a zone of inhibition of growth around Alphazurine A disc.

The use of Alphazurine discs, mannitol salt agar, and Novobiocin resistance permitted the presumptive differential diagnosis of the most important Staphylococcus pathogens in humans. The following procedures were followed and results obtained:

PREPARATION OF ALPHAZURINE A CULTURE MEDIA

The formula is as follows:
1. Brain Heart Infusion Agar 52. grams
2. Distilled Water 1000 ml
3. Alphazurine A 200 mgm
(Adrich Chemical Company Milwaukee, Wis.)

Brain heart infusion agar was added to distilled water and boiled for one minute. The media was cooled to approximately 500° C. and Alphazurine A added. The media was agitated to insure complete solution of the dye. The media was poured into plastic Petri plates.

PREPARATION OF ALPHAZURINE A SENSITIVITY DISC

Alphazurine A, 700 mg, was dissolved in 100 ml of sterile distilled water. Sterile paper ¼ inch discs were soaked for 2 hours in the dye solution. The excess solution was decanted and the discs dried at room temperature.

METHODS AND RESULTS

EXAMPLE 1: ALPHAZURINE A CULTURE MEDIA

A suspension of Staphylococci in a concentration of 0.5 McFarland unit was made in distilled water. The bacterial suspension was streaked on the Alphazurine A culture media plate with a swab, and the plate incubated for 24 hours at 37° C.

*Staphylococcus aureus* was inhibited or did not grow on the Alphazurine A culture plate, whereas *Staphylococcus epidermidis* and *Staphylococcus saprophyticus* grew profusely.

EXAMPLE 2: ALPHAZURINE A SENSITIVITY DISCS

*Staphylococcus aureus* suspension in distilled water in a concentration of 0.5 McFarland unit was made. The bacterial suspension was streaked on a Mueller-Hinton agar plate. After five minutes, an Alphazurine A disc was placed on the surface of the media, pressed down, and the plate inoculated at 37° C. for 24 hours. *Staphylococcus aureus* was sensitive to the Alphazurine A and produced a zone of inhibition of the bacteria of 10 to 16 mm in diameter. The zone was clear and sharply demarcated.

*Staphylococcus saprophyticus* was resistant.

*Staphylococcus epidermidis* produced a zone of inhibition of bacterial growth to a small degree. The zone of inhibition was 7 mm or less and the zone of demarcation was feathered and not sharp.

SUMMARY OF TEST RESULT

|  | Staphylococcus Aureus | Staphylococcus Epidermidis | Staphylococcus Saprophyticus |
|---|---|---|---|
| Alphazurine A Sensitivity | + | − | − |
| Utilization of Mannitol (acid production) | + | − | variable |
| Novobiocin | − | − | + |

The following additional examples further demonstrate that growth of *Staphylococcus aureus* is inhibited, and that growth of *Staphylococcus saprophyticus* and *Staphylococcus epidermidis* is not inhibited in liquid culture media containing alphazurine A:

EXAMPLE 3: BRAIN HEART INFUSION

Brain heart infusion media was obtained from Becton-Dickinson Microbiology Systems, Cockneysville, Md. The media has the following formula (Ref. 4).

| Brain Heart Infusion from Solids | 6.0 g |
|---|---|
| Peptic Digest of Animal Tissue | 6.0 g |
| Sodium Chloride | 5.0 g |
| Dextrose | 3.0 g |
| Pancreatic Digest of Gelatin | 14.5 g |
| Disodium Phosphate | 2.5 g |

The manufacturers directions were to suspend 37 grams of the dehydrated media in one liter of purified water. It was mixed thoroughly and boiled for one minute to completely dissolve the powder, then sterilized by autoclaving at 121° C. for 15 minutes.

In the experiment, the amount of Brain Heart Infusion was reduced to one-tenth of the amount used for 1000 ml. The alphazurine A- Brain Heart Infusion media was prepared by dissolving 3.7 grams of the media and 2 grams of alphazurine A (Aldrich Chemical Co. Inc., Milwaukee, Wis.), in 100 ml of purified water.

The alphazurine A-Brain Heart Infusion media was thoroughly mixed and boiled for one minute to completely dissolve the powder and the dye. Five ml of alphazurine A-Brain Heart Infusion media was placed in glass culture tubes and sterilized by autoclaving at 121° C. for 15 minutes. Colonies of *S. aureus*, American Type Culture Collection, number 25923, *S. saprophyticus* ATCC number 15305 and *S. epidermidis* ATCC number 12228 were suspended in sterile water to give a concentration equal of a 0.5 McFarland turbidity standard. One-tenth ml of each of the staphylococcal suspensions were added to 5 ml of the sterile alphazurine A-Brain Heart Infusion media. By this method approximately equal concentrations of each staphylococcus were added to the media. The inoculated media was incubated at 37° C.

At the end of 24, 48, and 72 hours incubation, the inoculated alphazurine A-Brain Heart Infusion media was subcultured by streaking 0.001 ml of each culture with a calibrated loop onto Trypticase soy agar with 5% sheep blood plates. The streaking was done in a cross-hatch manner in three planes to insure isolated colonies. Subculture of *Staphylococcus aureus* showed marked inhibition of growth in 24 and 48 hours, whereas there was no inhibition of growth of *S. saprophyticus* and *S. epidermidis*. After 72 hours of incubation in alphazurine A-Brain Heart Infusion media, *S. aureus* was completely inhibited whereas *S. saprophyticus* and *S. epidermidis* culture plates showed abundant growth.

EXAMPLE 4: MUELLER-HINTON BROTH

Mueller-Hinton Broth media was obtained from Becton-Dickinson Microbiology Systems, Cockneysville, Md.

| Beef Extract | 3.0 g |
|---|---|
| Acid Hydrolysate of Casein | 17.5 g |
| Starch | 1.5 g |

The media was prepared according to the manufacturers directions which are according to those for preparing Brain Heart Infusion agar described in Example 3. Alphazurine A-Mueller-Hinton Broth media was prepared by adding 2 grams alphazurine A and 2.2 grams of dehydrated media to 100 ml of purified water. Five ml of the prepared media were placed in culture tubes and sterilized as described in Example 3. Bacteria suspensions of *S. aureus, S. saprophyticus* and *S. epidermidis* were prepared to equal a 0.5 McFarland standard. One-tenth ml of each of the bacteria suspension were inoculated into the alphazurine A-Mueller-Hinton Broth media. After 24, 48, and 72 hours incubation at 37° C., subcultures were made on Trypticase soy agar with 5% sheep blood. The results were similar to those obtained in Example 3. *Staphylococcus aureus* was inhibited and the *Staphylococcus saprophyticus* and *Staphylococcus epidermidis* were not inhibited. *S. aureus* showed no growth after 72 hours, whereas *S. saprophyticus* and *S. epidermidis* showed abundant growth.

EXAMPLE 5: ANTIBIOTIC ASSAY BROTH

This media was obtained from Becton-Dickinson Microbiological Systems, Cockneysville, Md. (Ref. 6). The formula is as follows:

| Pancreatic Digest of Gelatin | 5.0 g |
|---|---|
| Yeast Extract | 1.5 g |
| Beef Extract | 1.5 g |
| Sodium Chloride | 3.5 g |
| Dextrose | 1.0 g |
| Dipotassium Phosphate | 3.68 g |
| Monopotassium Phosphate | 1.32 g |

Alphazurine A-Antibiotic Assay Broth culture media was prepared as described in Examples 3 and 4. Bacterial suspensions, primary inoculations, and subcultures were performed according to the methods described in Examples 3 and 4.

The results were the same as in Examples 3 and 4.

It will be understood by those of ordinary skill in the art that, while the above examples are illustrative of the present invention, other procedures and techniques generally known in the art, and variations thereof, for identifying and differentiation microorganisms by selectively culturing those microorganisms are appropriate and useful in the present invention and are considered to be within the scope thereof.

What is claimed is:

1. A procedure for identifying *Staphylococcus aureus* and differentiating it from coagulase negative staphylococci which comprises first culturing a microorganism suspected of being *Staphylococcus aureus* in the presence of Alphazurine A dye, then placing said suspected microorganism on a solid media and visually observing the presence or absence of growth or inhibition of growth of said microorganism on said solid media, the absence of growth or inhibition of growth being a positive indication of *Staphylococcus aureus*.

2. The procedure of claim 1 wherein said suspected microorganism is first cultured in a liquid culture medium containing said Alphazurine A dye, incubated and then subcultured on said solid media where said presence or absence of growth or said inhibition of growth of the microorganism is observed.

3. The procedure of claim 2 wherein said culturing of the suspected microorganism in the presence of Alphazurine A dye and said observing of the presence or absence or inhibition of growth take place on said solid media.

* * * * *